United States Patent [19]

Flick et al.

[11] Patent Number: 5,866,734
[45] Date of Patent: Feb. 2, 1999

[54] HYDROGENATION PROCESS

[75] Inventors: Klemens Flick, Herxheim; Cristina Freire Erdbrügger, Freinsheim; Franz Josef Bröcker; Gerald Meyer, both of Ludwigshafen; Ekkehard Schwab, Neustadt; Christof Herion, Ladenberg, all of Germany

[73] Assignee: Aktiengesellschaft, Ludwigshafen, Germany

[21] Appl. No.: 923,899

[22] Filed: Sep. 4, 1997

[30] Foreign Application Priority Data

Sep. 5, 1996 [DE] Germany ............. 196 360 64.1

[51] Int. Cl.$^6$ ................ C07C 5/02; C07C 7/167
[52] U.S. Cl. ................ 585/260; 589/262; 589/275; 589/277; 589/271
[58] Field of Search ............... 585/260, 261, 585/262, 273, 274, 275, 276, 277; 589/271

[56] References Cited

U.S. PATENT DOCUMENTS

| | | | |
|---|---|---|---|
| 4,260,840 | 4/1981 | Puls et al. | 585/259 |
| 4,839,329 | 6/1989 | Ihm et al. | 502/339 |
| 5,431,888 | 7/1995 | Hickey et al. | 422/191 |
| 5,431,890 | 7/1995 | Crossland et al. | 422/211 |
| 5,475,173 | 12/1995 | Cheung et al. | 585/259 |
| 5,595,634 | 1/1997 | Hearn et al. | 203/29 |

FOREIGN PATENT DOCUMENTS

| | | |
|---|---|---|
| 053 884 | 6/1982 | European Pat. Off. . |
| 061304 | 9/1982 | European Pat. Off. . |
| 64 301 | 11/1982 | European Pat. Off. . |
| 89 252 | 9/1983 | European Pat. Off. . |
| 259966 | 3/1988 | European Pat. Off. . |
| 288 362 | 4/1991 | European Pat. Off. . |
| 523 482 | 1/1993 | European Pat. Off. . |
| 653 243 | 5/1995 | European Pat. Off. . |
| 27 10 277 | 3/1977 | Germany . |
| 591211 | 1/1978 | U.S.S.R. . |
| 635081 | 11/1978 | U.S.S.R. . |
| 1 284 403 | 3/1961 | United Kingdom . |
| 1 299 629 | 12/1962 | United Kingdom . |
| 2 107 568 | 2/1971 | United Kingdom . |
| 31 19 850 | 2/1982 | United Kingdom . |
| 2094656 | 9/1982 | United Kingdom . |
| 95/21022 | 8/1995 | WIPO . |

OTHER PUBLICATIONS

*Pat. Abst. of Japan*, vol. 13, No. 260 (C–607), Jun. 15, 1989 (English abstract of JP 01 061433A, Mar. 8, 1989.

*Primary Examiner*—Bekir L. Yildirim
*Attorney, Agent, or Firm*—Keil & Weinkauf

[57] ABSTRACT

In a process for the hydrogenation of multiply unsaturated $C_2$–$C_8$ hydrocarbons, in particular $C_2$–$C_8$-alkynes and/or $C_4$–$C_8$-alkynenes and/or $C_4$–$C_8$-alkadienes in fluids comprising these by contact with a catalyst packing in the presence of free hydrogen, the catalyst packing can be produced by applying at least one substance which is active as catalyst and/or promoter to woven or knitted meshes or foils as support material.

10 Claims, No Drawings

HYDROGENATION PROCESS

The present invention relates to a process for hydrogenating $C_2$–$C_8$-alkynes and/or $C_4$–$C_8$-alkynenes and/or $C_4$–$C_8$-alkadienes in fluids comprising these. Alkynes, eg. acetylene, and dienes are undesired materials in many industrial syntheses because of their tendency to polymerize and their pronounced tendency to form complexes with transition metals. They sometimes have a very strong adverse effect on the catalysts used in these reactions. Thus, for example, the acetylene present in the $C_2$ stream of a steam cracker interferes with the polymerization of ethylene, so that the acetylene content of the $C_2$ stream has to be kept very small, preferably less than 1 ppm. The $C_3$ stream of a steam cracker, which comprises not only propylene but also from 2 to 3% of propadiene (PD) and about the same amount of propyne (methylacetylene, MA), also has to be purified before polymerization to give polypropylene. The typical content of multiply unsaturated hydrocarbons is here from about 4 to 6% by weight. A reduction of this content to a maximum of 10 ppm should preferably be achieved. The $C_4$ stream of a steam cracker also contains up to 70% of multiply unsaturated hydrocarbons. These are mainly butadiene, vinylacetylene and ethylacetylene. The total content of multiply unsaturated hydrocarbons should be reduced to less than 20 ppm, preferably a maximum of 10 ppm. This is achieved in industry by selective hydrogenation of the hydrocarbon streams over heterogeneous noble metal catalysts on ceramic supports. High demands are here placed on the hydrogenation catalysts used in respect of their selectivity and activity, since a very complete hydrogenation of the multiply unsaturated hydrocarbons without loss of monounsaturated hydrocarbons such as ethylene, propene or butenes is to be achieved.

In some cases, a raw $C_4$ stream from a steam cracker, which contains from about 40 to 60% by weight of butadiene, is to be selectively hydrogenated to form butenes in as high as possible a yield. In this case too, industrial heterogeneous noble metal catalysts on ceramic supports are used. For these applications, use is made of promoted or unpromoted noble metal catalysts on ceramic supports usually with palladium as active component in an amount of from 0.01 to 1% by weight.

In the known processes, carbon monoxide is often mixed into the reaction mixture for the hydrogenation of acetylene in order to increase the selectivity of the catalyst. The disadvantage of this method is that the selectivity-increasing action of the carbon monoxide is strongly temperature-dependent. Large temperature gradients in the catalyst bed therefore result in a worsening of the selectivity. In addition, the relatively high working temperatures which are necessary when carbon monoxide is added favor the increased formation of undesired polymers (green oil).

The known catalysts for the selective hydrogenation of multiply unsaturated compounds are generally prepared by impregnation of an inert support with an aqueous solution of a palladium salt, a mixture of a palladium salt with a promoter salt or by successive separate impregnation with aqueous solutions of the substances active as catalyst and/or promoter, subsequent drying and calcination at relatively high temperatures. Most of the available catalysts are reduced with hydrogen after installation in the reactor.

DE-A 2 107 568 describes a process for purifying hydrocarbons by selective hydrogenation. Multiply unsaturated compounds such as methylacetylene and propadiene are hydrogenated in the liquid phase in two reaction zones connected in series. In the first reaction zone, part of the liquid evaporates. The catalyst used is Pd on $Al_2O_3$.

EP-A-0 653 243 describes supported catalysts which are obtained by dissolving palladium nitrate solution, possibly together with silver nitrate solution, in a solvent, admixing the solution with a high molecular weight sodium polyacrylate and mixing with aluminum oxide as support. The composition obtained is shaped, dried and calcined. The catalyst is used for the selective hydrogenation of methylacetylene and propadiene in a $C_3$ stream in the liquid phase.

EP-A-0 532 482 describes a process for the selective hydrogenation of butadiene-rich raw $C_4$ fractions. The selective hydrogenation of butadiene to butenes is carried out in the liquid phase over fixed-bed supported palladium catalysts. The hydrogenation is carried out in two reaction zones connected in series.

DE-C-31 19 850 describes a process for the selective hydrogenation of butadiene in a $C_4$ fraction. The liquid-phase hydrogenation is carried out using 0.3% by weight of palladium on an aluminum oxide support in the form of spheres having a diameter of 2 mm.

EP-B-0 288 362 describes a process for the isomerization of 1-butene to 2-butenes in a $C_4$ hydrocarbon fraction comprising butadiene and sulfur-containing compounds. The hydrocarbon fraction is passed over a first bed of a catalyst comprising palladium and gold and/or platinum. The stream is then passed over a second catalyst bed comprising palladium deposited on aluminum oxide or on silicon dioxide.

U.S. Pat. No. 4,260,840 describes a process for purifying a stream comprising 1-butene. Here, butadiene is selectively hydrogenated to butene in a $C_4$ stream containing at least 30% by weight of 1-butene. As supported catalyst, use is made of Pd/Cr on aluminum oxide in a packed catalyst bed.

U.S. Pat. No. 5,475,173 describes a process for the selective hydrogenation of 1,3-butadiene. The catalyst comprises palladium and silver on $Al_2O_3$ and also an alkali metal fluoride.

EP-B-0 064 301 describes a catalyst for the selective hydrogenation of acetylene. The catalyst comprises from 0.01 to 0.025% by weight of palladium and from 2 to 6 times this amount of silver on an alpha-$Al_2O_3$ support having a surface area of from 3 to 7 $m^2/g$. The catalyst has a low CO-sensitivity and a long operating life.

EP-B-0 089 252 describes a catalyst for the selective hydrogenation of acetylenic hydrocarbons. The catalyst comprises from 0.03 to 1% by weight of palladium and from 0.003 to 0.3% by weight of gold on an $Al_2O_3$ support.

U.S. Pat. No. 4,839,329 describes a process for preparing a palladium catalyst on a titanium dioxide support. The palladium content is from 0.01 to 0.2% by weight. The catalyst is suitable for the selective hydrogenation of acetylene to ethene.

DE-C 1 284 403 describes a process for preparing palladium-heavy metal-alumina catalysts for the removal of acetylenes and diolefins from gas mixtures comprising predominantly monoolefins by selective hydrogenation. Pd/Cr on alumina-containing supports is used for removing methylacetylene and propadiene.

DE-C 1 299 629 describes a process for removing acetylenes from gas mixtures comprising predominantly olefins by selective hydrogenation. A Pd/Cr catalyst on alumina is likewise used for the gas-phase hydrogenation of propadiene and methylacetylene.

The known supported catalysts have the usual disadvantages of oxide-supported catalysts. They display abrasion, are sensitive to mechanical stress in the case of pressure pulses or the occurrence of a pressure drop over the catalyst bed and are unpleasant to handle when installing or removing fresh or spent catalyst.

Catalysis Today, 24 (1995), pages 181–187 describes the use of an $\alpha$-$Al_2O_3$ monolith having a wall thickness of 0.2 mm and a cell density of 110 cells/$cm^2$ for the selective hydrogenation of acetylene in the $C_2$ stream from a steam cracker in the gas and liquid phase.

A disadvantage of the ceramic monoliths is the absence of transverse mixing in the individual separated channels and the formation of laminar flows at low flow velocities, which leads to poorer selectivities.

It is an object of the present invention to provide catalysts for the selective hydrogenation of multiply unsaturated hydrocarbons in hydrocarbon streams. A further object of the present invention is the provision of a process for the hydrogenation of multiply unsaturated hydrocarbons which avoids the above-described disadvantages of the known catalysts.

We have found that these objects are achieved by a process for the hydrogenation of multiply unsaturated $C_2$–$C_8$ hydrocarbons, in particular $C_2$–$C_8$-alkynes and/or $C_4$–$C_8$-alkynenes and/or $C_4$–$C_8$-alkadienes in fluids comprising these by contact with a catalyst packing in the presence of free hydrogen, wherein the catalyst packing can be produced by applying at least one substance which is active as catalyst and/or promoter to woven meshes knitwear or foils as support material.

The catalysts used according to the present invention have the structure described below.

Support material

Support materials which can be used for the catalysts employed according to the present invention are many foils and woven meshes, as well as knitted meshes. According to the present invention it is possible to use woven meshes having different types of weave, for example smooth-surface woven mesh, twilled mesh, braid-woven mesh, five-shaft satin-woven mesh or other special types of weave. Suitable woven wire meshes are, according to one embodiment of the invention, meshes made of weavable metal wires such as iron, spring steel, brass, phosphor bronze, pure nickel, Monel metal, aluminum, silver, nickel silver, nickel, Nichrome, chromium steel, stainless, acid-resistant and high-temperature-resistant chromium-nickel steels and also titanium. The same applies to knitted meshes.

It is likewise possible to use woven or knitted meshes of inorganic materials, for example of $Al_2O_3$ and/or $SiO_2$.

Synthetic wires and woven meshes made of plastics can also be used according to an embodiment of the invention. Examples are polyamides, polyesters, polyvinyls, polyolefins such as polyethylene, polypropylene, polytetrafluoroethylene and other plastics which can be processed into woven or knitted meshes.

Preferred support materials are metal foils or woven metal meshes, for example stainless steels having the material numbers 1.4767, 1.4401, 2.4610, 1.4765, 1.4847, 1.4301, etc. The designation of these materials by the material numbers mentioned is according to the material numbers in the "Stahleisenliste", published by the Verein Deutscher Eisenhüttenleute, 8th edition, pages 87, 89 and 106, Verlag Stahleisen mbH, Düsseldorf, 1990. The material number 1.4767 is also known under the name Kanthal.

The metal foils and woven metal meshes are particularly suitable since they can be roughened by heating the surface before coating with catalytically active compounds or promoters. For this purpose, the metallic supports are heated at from 400° to 1100° C., preferably from 800° to 1000° C., for from 0.5 to 24 hours, preferably from 1 to 10 hours, in an oxygen-containing atmosphere such as air. According to an embodiment of the invention, this pretreatment can be used to control or increase the activity of the catalyst.

Coating of the catalyst support

According to the present invention, the catalyst supports used according to the present invention can be coated by means of various methods with catalytically active compounds and promoters.

According to one embodiment of the invention, the substances which are active as catalyst and/or promoter are applied by impregnation of the support in bulk, by electrochemical deposition or deposition in the presence of a reducing agent (electroless deposition).

The catalyst mesh or catalyst foil can then, according to an embodiment of the invention, be shaped to form monoliths for installation in the reactor. According to a further embodiment of the invention, the shaping can also be carried out before application of the active substances or promoters.

According to an embodiment of the invention, the catalyst supports which can be used according to the present invention, in particular the woven or knitted meshes and foils, can be coated with "thin layers" of catalytically active compounds and promoters by means of a vacuum vapor deposition technique. For the purposes of the present invention, "thin layers" are coatings in the thickness range from a few Å ($10^{-10}$m) to a maximum of 0.5 μm. As vacuum vapor deposition techniques, various processes can be employed according to the present invention. Examples are thermal vaporization, flash vaporization, cathode atomization (sputtering) and the combination of thermal vaporization and cathode atomization. Thermal vaporization can here be carried out by means of direct or indirect electric heating.

Vaporization by means of an electron beam can likewise be used according to the present invention. For this purpose, the substance to be vaporized is heated on the surface in a water-cooled crucible by means of an electron beam so strongly that even high-melting metals and dielectrics are vaporized. According to an embodiment of the invention, chemical reactions can be effected during buildup of the layers by vapor deposition techniques by means of targeted additions of suitable amounts of reactive gases to the residual gas. A suitable reaction procedure thus enables oxides, nitrides or carbides to be produced on the support.

Using the process of the present invention, the supports, in particular the woven or knitted meshes and foils, can be treated with vapor batchwise or continuously in a vacuum vapor deposition unit. For example, the vapor treatment is carried out by heating the catalytically active component or compound to be applied, for example a noble metal, in a vacuum of from $10^{-2}$ to $10^{-10}$ torr preferably from $10^{-4}$ to $10^{-8}$ torr, by means of an electron beam so strongly that the metal is vaporized out of the water-cooled crucible and is deposited on the support. The support mesh or knitwear is advantageously arranged such that as great as possible a part of the vapor stream condenses on the support. The meshes or knitwear can here be coated continuously by means of a winding machine. According to the present invention, preference is given to continuous sputtering in an air-to-air unit.

Suitable parameters and conditions for the vacuum vapor deposition techniques may be found, for example, in "Handbook of Thin Film Technology", Maissel and Glang, McGraw Hill, New York, 1970, "Thin Film Processes" by J. L. Vossen and B. Kern, Academic Press, New York, and also EP-A 0 198 435. EP-A-0 198 435 discloses the production of a catalyst mesh packet by vapor deposition of platinum or platinum and rhodium onto stainless steel mesh.

In the production of the catalyst according to the present invention by vacuum vapor deposition techniques, polycrystalline particles which are as disordered and disrupted as possible should be produced on the support and the predominant proportion of the atoms of the particles should be on the surface. The vacuum vapor deposition technique employed here is thus different from the known vapor deposition techniques in the optical and electrical industries in which a high purity of the support and vapor-deposited materials has to be ensured and a predetermined condensation temperature on the support as well as a particular vapor deposition rate has to be set.

In the process of the present invention, it is possible for one or more catalytically active compounds or promoters to be vapor-deposited.

According to one embodiment of the invention, the coatings of catalytically active substance are preferably in the thickness range from 0.2 nm to 100 nm, particularly preferably from 0.5 nm to 20 nm, in particular from 3 to 7 nm.

According to an embodiment of the invention, catalytically active compounds used are the elements of transition group VIII of the Periodic Table of the Elements, preferably nickel, palladium and/or platinum, in particular palladium. Promoters can be present according to one embodiment of the invention and can be selected according to the present invention from, for example, the elements of main groups III, IV, V and VI and also transition groups I, II, III, VI and VII of the Periodic Table of the Elements.

The promoter which is used according to one embodiment of the invention is preferably selected from the group consisting of copper, silver, gold, zinc, chromium, cadmium, lead, bismuth, tin, antimony, indium, gallium, germanium, tungsten or mixtures thereof, particularly preferably silver, indium and germanium, copper, gold, zinc, chromium, cadmium, lead, bismuth, tin, antimony. The layer thickness of the promoter or promoters used according to one embodiment of the invention is from 0.1 to 20 nm, preferably from 0.1 to 10 nm, in particular from 0.5 to 3 nm.

Before the application of the catalytically active substance and/or the promoter, the support can be modified by vapor deposition of a layer of is an oxidizable metal and subsequent oxidation to form an oxide layer. According to one embodiment of the invention, the oxidizable metal used is magnesium, aluminum, silicon, titanium, zirconium, tin or germanium or a mixture thereof. The thickness of such an oxide layer is, according to the present invention, in the range from 0.5 to 200 nm, preferably from 0.5 to 50 nm.

The coated support material can be heat-treated after coating, for example a palladium-coated support material at from 200° to 800° C., preferably from 300° to 700° C., for from 0.5 to 2 hours.

After the catalyst has been produced, it can, if desired or necessary, be reduced with hydrogen at from 20° to 250° C., preferably from 100° to 200° C. This reduction can also be carried out in the reactor itself, which is preferred.

According to an embodiment of the invention, the catalysts can be built up systematically, for example in a vapor deposition unit using a plurality of different vaporization sources. Thus, for example, an oxide layer or, by reactive vapor deposition, a bonding layer can first be applied to the support. Catalytically active components and promoters can be vapor-deposited on this base layer in a plurality of alternating layers. Introducing a reactive gas into the receptacle during vapor deposition enables promoter layers of oxides and other compounds to be produced. Heat-treatment steps can also be carried out in between or subsequently.

The substance or substances active as catalyst and/or promotor can also be applied by impregnation.

The catalysts produced by vapor deposition according to the present invention, in particular catalyst meshes, catalyst knitwear and catalyst foils, have very good adhesion of the catalytically active compounds or promoters. They can therefore be shaped, cut and, for example, processed into monolithic catalyst elements without the catalytically active compounds or promoters being detached. Catalyst packings of any shape for a reactor, eg. flow-through reactor, a reaction column or distillation column can be produced from the catalyst meshes, catalyst knitwear and catalyst foils of the present invention. It is possible to produce catalyst packing elements having different geometries, as are known from distillation and extraction technology. Examples of advantageous catalyst packing geometries according to the present invention which offer the advantage of a low pressure drop in operation are those of the structural type Montz A 3 and Sulzer BX, DX and EX. An example of a catalyst geometry according to the present invention made of catalyst foils or expanded metal catalyst foils are those of the type Montz BSH.

The amount of catalyst, in particular amount of catalyst mesh, catalyst knitwear or amount of catalyst foil, processed per unit volume can be controlled within a wide range, whereby a different size of the openings or channel widths in the catalyst mesh or catalysr knitwear or in the catalyst foil is obtained. Appropriate selection of the amount of catalyst mesh, catalyst knitwear or catalyst foil per unit volume enables the maximum pressure drop in the reactor, eg. flow-through or distillation reactor, to be set and thus enables the catalyst to be matched to experimentally determined requirements.

The catalyst used according to the present invention preferably has a monolithic form as is described, for example, in EP-A-0 564 830. Further suitable catalysts are described in EP-A-0 218 124 and EP-A-0 412 415.

A further advantage of the monolithic catalysts used according to the present invention is the good fixability in the reactor bed, so that, for example, they can be used very well in hydrogenations in the liquid phase in the upflow mode at a high cross-sectional loading. In comparison, in the case of conventional catalyst supports there is the danger of fluidization in the catalyst bed which can lead to possible abrasion or disintegration of the shaped bodies. In gas-phase hydrogenation, the catalyst packing is capable of withstanding shock or vibrations. No abrasion occurs.

Hydrogenation

The above-described catalysts are used according to the present invention in processes for the hydrogenation, in particular selective hydrogenation, of multiply unsaturated $C_2$–$C_8$-hydrocarbons in fluids comprising these. The multiply unsaturated hydrocarbons can be, for example, $C_2$–$C_8$-alkynes, $C_4$–$C_8$-alkynenes, $C_4$–$C_8$-alkadienes or mixtures of these. They are preferably unsaturated $C_2$–$C_6$-hydrocarbons, in particular $C_2$–$C_4$-hydrocarbons.

According to an embodiment of the invention, these multiply unsaturated hydrocarbons are present in $C_2$, $C_3$, $C_4$, $C_5$ or $C_6$ streams, preferably in streams from a steam cracker or catalytic cracker. These streams generally comprise, as described above, more or less large amounts of the corresponding multiply unsaturated $C_2$–$C_6$-hydrocarbons.

By using the catalysts of the present invention, these compounds can be converted into the corresponding monounsaturated hydrocarbons with high selectivity and in high yield.

The selective hydrogenations are, according to the present invention, carried out either adiabatically or isothermally in the gas or liquid phase. The number of reactors depends on the amount of compounds to be hydrogenated in the gas stream or liquid stream. For example, an adiabatically operated reactor suffices for contents below 1% by weight in gas-phase hydrogenations, with the hydrogen/multiply unsaturated hydrocarbon ratio being from about 1.8 to 2. If the content of multiply unsaturated compounds is higher, the hydrogenation is carried out in two or more reactors connected in series. In this case, the hydrogen is fed in before each reactor.

The hydrogenation of a $C_3$ stream in the gas phase is usually carried out in three reactors connected in series, with a conversion of from 60 to 70% being achieved in the first reactor and a conversion of from 30 to 40% being achieved in the second reactor. The remaining conversion is achieved in the third reactor, or the third reactor serves as a safety reactor.

In the case of hydrogenation in the liquid phase, an adiabatically operated reactor without recirculation suffices for contents of multiply unsaturated hydrocarbons of up to 3.3% by weight. At a hydrogen/multiply unsaturated hydrocarbon ratio of from about 1 to 1.5, this gives a depletion down to from 500 to 1000 ppm in the output, which corresponds to a conversion of from 95 to 99%. If the content of multiply unsaturated hydrocarbons is higher, recirculation is generally necessary. If the content of multiply unsaturated hydrocarbons in the output is to be reduced to less than 10 ppm, the hydrogenation is generally carried out in two reactors connected in series, with the hydrogen being fed in before each reactor as described above. At a hydrogen/unsaturated hydrocarbon ratio of from about 4 to 8, a total conversion of more than 99.9% is achieved in the second reactor.

In the hydrogenation of $C_2$ streams having acetylene contents of more than 2% by weight, the hydrogenation is usually carried out in one isothermal reactor and one or two adiabatic reactors connected to the isothermal reactors.

In the liquid-phase hydrogenation of a $C_4$ stream with high content of butadiene, one or two stages are provided depending on the desired butadiene depletion. Above a depletion factor of about 200, a two-stage process is generally preferred. Thus, for example, the selective hydrogenation of a raw $C_4$ stream from a steam cracker containing about 45% by weight of butadiene is carried out in two stages to a residual butadiene content of less than 10 ppm.

It is as well possible to remove low contents of butadiene selectively in as so called remainder hydrogenation. In this case a one step process with depletion factors of more than 1000 is accessible. For example the hydrogenation of 0,5% by weight of butadiene to values below 10 ppm is performed in a one step process, wherein at the same time a maximum of butene-1 present can be retained.

According to one embodiment of the invention, the hydrogenation is carried out in the gas phase. In particular, the hydrogenation of $C_2$ and/or $C_3$ streams is carried out in the gas phase. Examples of reactors which can be used are tube reactors and shaft reactors as well as tube-bundle reactors.

According to one embodiment of the invention, a plurality of tube reactors can be connected in series. Here, according to one embodiment of the invention, the hydrogen is fed in before each reactor. For a further description of reactors which are suitable according to the present invention, reference is made to the introduction.

The selective hydrogenation in the gas phase is, according to one embodiment of the invention, carried out at pressures of from 5 to 50 bar, preferably from 10 to 30 bar, in particular from 15 to 25 bar. According to one embodiment of the invention, the space velocities are from 500 to 8000 $m^3/m^3$ h, preferably from 1000 to 5000 $m^3/m^3$ h, in particular from 2000 to 4000 $m^3/m^3$ h. The inlet temperature for the hydrogenation is, according to one embodiment of the invention, from $-20°$ to $150°$ C., preferably from $20°$ to $120°$ C., in particular from $20°$ to $80°$ C. It is possible to use an adiabatically operated or an isothermally operated reactor. The hydrogenation can likewise be carried out in a plurality of reactors connected in series, these being operated isothermally or adiabatically. For example, two adiabatic reactors can follow one isothermal reactor, particularly in the hydrogenation of a $C_2$ stream.

According to an embodiment of the invention, the hydrogenation is carried out in the liquid phase or in a mixed liquid/gas phase with at least 50% by weight of the hydrocarbon stream in the liquid phase. Here, according to an embodiment of the invention, the hydrogenation can be carried out in the downflow mode or in the upflow mode. In the upflow made the hydrogen added can be present as a solution in the liquid phase. Reactors which can be used here are, for example, tube reactors or tube-bundle reactors.

According to one embodiment, the hydrogenation is carried out at a pressure of from 5 to 70 bar, preferably from 5 to 40 bar, in particular from 10 to 30 bar. According to one embodiment of the invention, the space velocity is from 1 to 100 $m^3/m^3$ h, preferably from 2 to 40 $m^3/m^3$ h, in particular from 2 to 20 $m^3/m^3$ h. The inlet temperature for the hydrogenation is, according to one embodiment of the invention, from $-10°$ to $150°$ C., preferably from $0°$ to $120°$ C., in particular from $0°$ to $90°$ C. In order to ensure the formation of a liquid phase, it is necessary to select suitable temperature and pressure parameters which are dependent on the mixture of substances used in each case.

According to an embodiment of the invention, the hydrogenation is carried out in a catalytic distillation process. In this process, the hydrogenation as described above is combined with simultaneous distillation or rectification over the catalyst packing.

In such a process, the hydrogenation and a distillation take place simultaneously or immediately after one another. At least one component of the reaction mixture is distilled from the hydrogenation mixture after the hydrogenation. The term "catalytic distillation" refers to a chemical reaction, here a hydrogenation, which is combined with a distillation or rectification in a suitable apparatus. As reactor for the catalytic distillation, it is possible to use any suitable distillation apparatus in which the catalyst packing can be installed in the distillation part. This is possible, for example, by installation of the catalyst packing in a distillation column in the distillation apparatus.

The reaction mixture, ie. the hydrocarbon stream, is introduced into the distillation apparatus at a suitable point, according to one embodiment into the bottom of the distillation apparatus. This is particularly advantageous in the hydrogenation of a $C_3$, $C_4$, $C_5$ or $C_6$ stream. The hydrogenated components and the alkenes are here taken off at the top of the distillation apparatus.

Preferably the hydrogenation is proceeds selectivetly and essentially no hydrogenation of alkenes to alkanes occnos.

The invention is illustrated by the following examples.

In the performance tests for hydrogenation in the gas phase, the monolithic catalysts were used in an unpressurized laboratory apparatus or in a pilot part apparatus under increased pressures. The temperatures of the gas mixture entering the hydrogenation zone are generally from $15°$ to about $120°$ C., preferably from $25°$ to $90°$ C. The volume ratio of hydrogen to the multiply unsaturated hydrocarbons is generally from 0.5:1 to 2.5:1, in the $C_2$ hydrogenation preferably from 1.1:1 to 2:1, in particular from 1.2:1 to 1.8:1, and in the first stage of the $C_3$ hydrogenation from 0.5:1 to 0.8:1.

In the following, proportions by volume of gas are proportions by volume at STP.

EXAMPLE 1

Plain-woven wire mesh made of material No. 1.4301 and having a mesh opening of 0.125 mm and a wire diameter of 0.1 mm was heated in air at $800°$ C. for 3 hours. After cooling, the support mesh which had been pretreated in this way had first 6 nm of Pd and then 1 mm of Ag vapor-deposited on both sides in an electron beam vapor deposition unit at a pressure of from 1 to $3 \times 10^{-6}$ torr. The thickness of the layers was measured by means of a crystal oscillator and the vapor deposition rate was controlled using the crystal oscillator. The amount of palladium deposited was 138 $mg/m^2$ and the amount of silver was 19.5 $mg/m^2$. The catalyst mesh thus produced was fabricated into 3 monoliths having a height of 90 mm and a diameter of 18.6 mm. In the middle of the monoliths there was a thermocouple hole having a diameter of 4 mm. To produce the monoliths, mesh strips having a width of 92 mm and a length of 37.5 cm were cut and one of these was corrugated by means of a toothed roller (modulus 0.5 mm). This corrugated mesh was laid together with the smooth mesh and wound around a 4 mm thick metal rod. This gave a monolithic catalyst which was strengthened by point welding at the outer edge.

EXAMPLE 2

Gas-phase hydrogenation of a $C_3$ stream under pressure

Three monoliths produced as described in Example 1 and having a total surface area of 4219 $cm^2$ were installed in a reactor for the test on the gas-phase hydrogenation of methylacetylene and propadiene in a $C_3$ stream from a steam cracker. A multiple thermocouple was introduced axially into the 4 mm wide thermocouple hole.

The process conditions were set according to the conditions in a first stage of the usually 3-stage selective hydrogenation of methylacetylene and propadiene in the $C_3$ stream.

The reactor had a diameter of 18.6 mm and a length of 2 m. The catalyst monolith had a height of 27 cm and a volume of 70 ml.

After flushing with nitrogen and hydrogen at 120° C., 660 g/h of a gas mixture composed of 6.8% of propane, 1.7% of propadiene and 2.2% of methylacetylene in propylene were mixed with differing amounts of hydrogen and passed over the catalyst at an inlet temperature of 50° C. and a pressure of 10 bar. The compositions of the reaction product are summarized in the table below.

TABLE 1

| $H_2$ [l/h] | $H_2$/ MA PD | Propane % by volume | Propene % by volume | Propadiene % by volume | Propine % by volume | C6+ % by volume | Conversion (MAPD) [%] | S(propene) [%] |
| --- | --- | --- | --- | --- | --- | --- | --- | --- |
| 8.1 | 0.5 | 6.848 | 91.52 | 0.737 | 0.67 | 0.22 | 64 | 90 |
| 8.9 | 0.55 | 6.895 | 91.61 | 0.653 | 0.594 | 0.244 | 68 | 88 |
| 9.7 | 0.6 | 6.962 | 91.67 | 0.567 | 0.53 | 0.262 | 72 | 86 |
| 11.3 | 0.7 | 7.161 | 91.72 | 0.439 | 0.439 | 0.268 | 78 | 81 |

MAPD is the mixture of multiply unsaturated hydrocarbons, namely methylacetylene and propadiene. The ratio of hydrogen to MAPD is the volume ratio. S is the selectivity based on propene.

Under the conditions of the first hydrogenation stage, the catalyst has very high selectivities.

EXAMPLE 3

Plain-woven wire mesh made of material No. 1.4767 and having a mesh opening of 0.18 mm and a wire diameter of 0.112 mm was heated in air at 900° C. for 5 hours. After cooling, the support mesh which had been pretreated in this way had first 92 mg of Pd/m² and then 26.4 mg of Zn/m² vapor deposited under the same conditions on both sides in an electron beam vapor deposition unit at a pressure of $1\times10^{-6}$ torr. As described in Example 1, a wound 126 cm³ monolith was produced from the catalyst mesh thus obtained.

EXAMPLE 4

Pressureless $C_2$ gas-phase hydrogenation

The catalyst monolith obtained as described in Example 3 was installed in a tube reactor as described in Example 2. The test of the catalyst was carried out under atmospheric pressure using a gas mixture of 1% by volume of acetylene, 2% by volume of hydrogen and 97% by volume of ethylene at a space velocity over the catalyst of 3000 m³/m³(cat) h. At 82° C., an acetylene conversion of 70% was achieved at a selectivity to ethylene of 97%. Under otherwise identical reaction conditions, a commercial supported catalyst containing 0.02% by weight of Pd and 0.01 % by weight of Zn gave a selectivity to ethylene of only 62% at a conversion of 70%.

EXAMPLE 5

The support material used was the material described in Example 3 which was pretreated by heating in air at 900° C. and subsequently had 138 mg/m² of palladium vapor-deposited onto it using a method similar to Example 3. Rolling together one corrugated and one smooth strip of catalyst mesh having a width of 10 cm produced a monolith having a 5 mm thermocouple hole. The resulting monolith had a volume of 71.6 cm³ and comprised 15.25 dm² of catalyst mesh.

EXAMPLE 6

Gas-phase hydrogenation of a $C_2$ stream under a pressure of 20 bar

The catalyst monolith produced as described in Example 5 was installed in a tube reactor as described in Example 2. After flushing with nitrogen, the catalyst was reduced with 10 l/h of hydrogen for 3 hours at 150° C. At an inlet temperature of 82° C., 160 l/h of a gas mixture comprising 98.824% by volume of ethylene and 1.145% by volume of acetylene, which had been mixed with 1.46% by volume of hydrogen, were then passed over the catalyst. The reaction product comprised 99.394% by volume of ethylene, 0.486% by volume of ethane and 0.01% by volume of acetylene (conversion 99.1%, selectivity 58%). On increasing the hydrogen content to 1.67% by volume, the ethane content in the reaction product rose to 0.678% by volume. Acetylene could then no longer be detected (conversion 100%, selectivity 43%).

Addition of 1.5 ppm of carbon monoxide enabled the selectivity to be increased further. At an inlet temperature of 84° C., an acetylene-free reaction product was obtained. The ethylene content was 99.419% by volume, the ethane content was 0.442% by volume.

EXAMPLE 7

Using the method described in Example 1, 138 mg of Pd/m² and then 19.5 mg of Ag/m² were vapor-deposited on a supported mesh made of material No. 1.4767 which had been pretreated as described in Example 1 by heating in air at 900° C. The catalyst mesh was subsequently fabricated into a monolith having a volume of 126 cm³.

EXAMPLE 8

Pressureless gas-phase hydrogenation of a $C_2$ stream

The catalyst produced as described in Example 1 was used as described in Example 4 for the selective hydrogenation of acetylene. At a conversion of 70%, a selectivity to ethylene or 91% was achieved.

EXAMPLE 9

Liquid-phase hydrogenation of $C_3$ streams

The catalyst produced as described in Example 1 was used for the liquid-phase hydrogenation of methylacetylene and propadiene in a $C_3$ stream from a steam cracker. The process conditions were selected corresponding to the conditions of a first stage of the usually 2-stage hydrogenation of the $C_3$ stream.

3 of the monoliths produced as described in Example 1 and having a total surface area of 4219 cm$^2$ were installed in an adiabatically operated tube reactor having a diameter of 20 mm. A multiple thermocouple was introduced axially into the 4 mm wide thermocouple hole. To ensure good wetting of the catalyst, as is ensured in industrial reactors by the high cross-sectional loading, the upflow mode was employed. After flushing with nitrogen and hydrogen at 120° C., 520 g/h of a C$_3$ stream from a steam cracker composed of 6.8% by volume of propane, 1.7% by volume of propadiene and 2.2% by volume of methylacetylene in propylene and 13 standard l/h of hydrogen were passed over is the catalyst at an inlet temperature of 10° C. and a pressure of 23 bar. The reaction product comprised 7.3% by volume of propane and 0.3% by volume of unknowns (oligomers) in propylene. This corresponds to a selectivity to propylene of 80% at a conversion of more than 99.9%. The results are summarized in Table 2.

COMPARATIVE EXAMPLE 1

The catalyst produced as described in EP-A-0 653 243 was used as a comparative catalyst in the liquid-phase hydrogenation of methylacetylene and propadiene in the C$_3$ stream from a steam cracker. The process conditions were selected as in Example 9. 70 ml of the catalyst were installed in the adiabatically operated tube reactor. After flushing with nitrogen and hydrogen at 120° C., 520 g/h of a C$_3$ stream from a steam cracker composed of 5.1% by volume of propane, 1.8% by volume of propadiene, 2.3% by volume of methylacetylene in propylene and 13 standard l/h of hydrogen were passed over the catalyst at an inlet temperature of 10° C. and a pressure of 22 bar. The reaction product comprised 5.5% by volume of propane and 0.5% by volume of unknowns in propylene. The unknowns are oligomers formed. This corresponds to a selectivity to propylene of 78% at a conversion of greater than 99.9%. The results are summarized in Table 2.

COMPARATIVE EXAMPLE 2

The catalyst LD 265 described in Chem. Eng. Prog., 70 (1974), 74–80 was employed as a comparative catalyst for the liquid-phase hydrogenation of methylacetylene and propadiene in a C$_3$ stream from a steam cracker. The process conditions were selected as in Comparative Example 1, but the stream contained 8% of propane, 1.7% by volume of propadiene and 2.1% by volume of methylacetylene. The reaction product comprised 8.5% by volume of propane and 0.7% by volume of unknowns in propylene. This corresponds to a selectivity to propylene of 69% at a conversion of more than 99.9%. The results are summarized in Table 2.

TABLE 2

| Catalyst | Comparative Ex. 1 (0.3% Pd, 0.4 kg/l) | Comparative Ex. 2 (0.3% Pd, 0.7 kg/l) | Example 9 Pd/Ag-Catalyst |
|---|---|---|---|
| whsv [kg/l] | ca. 6.5 | ca. 6.5 | ca. 6.5 |
| Pressure [bar] | 22 | 22 | 22 |
| H$_2$/MAPD calc. [mol/mol] | 1.08 | 1.1 | 1.1 |
| T$_{in}$ [°C.] | 10 | 10 | 10 |
| MAPD [ppm] | <10 | <10 | <10 |
| S(propene) [%] | 78 | 69 | 80 |
| Conversion [%] | >99.9 | >99.9 | >99.9 |
| Δ Propane [%] | 0.5 | 0.5 | 0.5 |
| Δ Unknowns [%] | 0.5 | 0.7 | 0.3 |

In the table, whsv is the weight hourly space velocity in kg/l. MAPD is the amount of multiply unsaturated hydrocarbons, namely methylacetylene and propadiene. The indicated ratios of H$_2$/MAPD were calculated from the amounts of H$_2$ consumed in the reaction.

The table shows an increase in the selectivity from Comparative Example 2 through Comparative Example 1 to Example 9. Although the thin-layer catalyst employed in Example 9 contains only 28 mg of Pd and 4 mg of Ag in the amount of catalyst used and, for example, the catalyst in Comparative Example 2 contains 240 mg of Pd, it has a comparable activity and a higher selectivity. The formation of oligomers summarized as unknowns is lowest for the catalyst of the invention used in Example 9.

EXAMPLE 10

To produce the catalyst, a plain-woven wire mesh made of material No. 1.4767 and having a mesh opening of 0.18 mm and a wire diameter of 0.112 mm was heated in air at 900° C. for 5 hours. After cooling, 138 mg of Pd/m$^2$ of mesh were deposited on both sides of the support material at a pressure of 1×10$^{-6}$ torr. Monoliths were subsequently produced from this catalyst mesh. For this purpose, a 20 cm wide mesh strip was corrugated by means of a toothed roller (modulus 0.5 mm) and together with a smooth mesh was rolled up around a metal rod having a diameter of 4.5 mm to give a roll. The roll was strengthened by point welding at the outer edge and the metal rod was removed to leave the thermocouple hole. The monolithic catalyst thus obtained had a diameter of 16 mm and a height of 20 cm. The amount of catalyst mesh in a monolith was 940 cm$^2$ and 5 monoliths were installed in the hydrogenation reactor.

EXAMPLE 11

Liquid-phase hydrogenation of raw C$_4$ fraction from a steam cracker.

The selective hydrogenation of a raw C$_4$ fraction was carried out over the catalyst from Example 10 in a fixed-bed reactor of a pilot plant unit which was fitted with a separator and a liquid circuit. The fixed-bed reactor was able to be heated by means of electric heating and had a diameter of 16 mm and a length of 2 m. The starting material was metered into the circulating stream by means of a pump and mixed with the necessary hydrogen at a mixing point. The selective hydrogenation was carried out in a fixed bed comprising the monolithic catalyst described in Example 10. The reaction mixture subsequently went to a separator in which the gas and liquid phases were separated. The major part of the liquid phase was circulated. A smaller part corresponding to the amount of starting material was continuously taken from the system and analyzed by gas chromatography.

Before commencement of the experiment, the installed monolithic catalyst was reduced with hydrogen at 120° C. and 5 bar pressure for 12 hours. The unit was subsequently run up using hydrogenated C$_4$ fraction and hydrogen. The results of the experiment on the selected hydrogenation are summarized in Table 3 below.

TABLE 3

|  | Starting material | Pd catalyst from Example 10 Hydrogenation product | |
|---|---|---|---|
| Space velocity [m$^3$/m$^3$h] |  | 9.0 | 9.0 |
| Recycle/Feed |  | 8.2 | 8.2 |
| T$_{in}$ [°C.] |  | 60 | 60 |
| p [bar] |  | 17.7 | 18.3 |
| Ratio of H$_2$/(butadiene + butenyne + butyne) |  | 0.98 | 1.02 |
| Butadiene + butenyne + Butyne [% by weight] | 34.9 | 1.8 | 0.5 |
| 1-butene [% by weight] | 14.2 | 40.3 | 39.5 |

TABLE 3-continued

|  | Starting material | Pd catalyst from Example 10 Hydrogenation product |
|---|---|---|
| 2-trans-butene [% by weight] | 4.5 | 17.6 | 18.6 |
| 2-cis-butene [% by weight] | 3.3 | 5.7 | 6.2 |
| i-butene [% by weight] | 23.6 | 23.6 | 23.6 |
| i-butane [% by weight] | 3.0 | 3.0 | 3.0 |
| n-butane [% by weight] | 7.2 | 7.7 | 8.3 |
| $C_5$ hydrocarbons [% by weight] | 0.3 | 0.3 | 0.3 |
| Conversions [%] |  | 95.9 | 98.9 |
| Total butene selectivity [%] |  | 98.8 | 97.5 |

The catalyst displayed a very high activity. High conversions could be achieved even at high space velocities. Even in a hydrogenation to a residual butadiene content of 1.8% by weight, the hydrogenation to n-butane was only 0.5% by weight. No hydrogenation of the i-butene took place.

EXAMPLE 12

To produce the catalyst, plain-woven wire mesh made of material No. 1.4767 and having a mesh opening of 0.18 mm and a wire diameter of 0.112 mm was heated in air at 1000° C. for 5 hours. After cooling, 92 mg of $Pd/m^2$ were vapor-deposited on both sides of the support material at a pressure of $1 \times 10^{-6}$ torr. To increase the selectivity, the Pd catalyst mesh was subsequently doped with 0.5 nm of germanium by vapor deposition. The thickness of the germanium doping layer was measured during the vapor deposition procedure using a crystal oscillator. 5 monoliths were fabricated as described in Example 10 from the catalyst mesh thus obtained and these were installed in the hydrogenation reactor.

EXAMPLE 13

Liquid-phase hydrogenation of raw $C_4$ fraction from a steam cracker

The catalyst described in Example 12 was likewise used in the unit described in Example 11. Before commencement of the experiment, the catalyst was reduced with hydrogen at 120° C. and 5 bar pressure for 12 hours in a similar way to Example 11. The unit was subsequently run up using hydrogenated $C_4$ fraction and hydrogen. The results of the experiment on the selective hydrogenation are summarized in Table 4 below.

TABLE 4

|  | Starting material | Pd/Ge catalyst from Example 12 |
|---|---|---|
| Space velocity [m³/m³h] |  | 9.0 |
| Recycle/Feed |  | 8.2 |
| $T_{in}$ [°C.] |  | 60 |
| p [bar] |  | 17.2 |
| Ratio of $H_2$/(butadiene + butenyne + butyne) |  | 0.97 |
| Butadiene + butenyne + Butyne [% by weight] | 46.4 | 2.4 |
| 1-butene [% by weight] | 15.2 | 42.5 |
| 2-trans-butene [% by weight] | 5.1 | 18.9 |
| 2-cis-butene [% by weight] | 3.8 | 6.3 |
| i-butene [% by weight] | 23.9 | 23.9 |
| i-butane [% by weight] | 1.0 | 1.0 |
| n-butane [% by weight] | 4.4 | 4.8 |
| $C_5$ hydrocarbons [% by weight] | 0.2 | 0.2 |
| Conversion [%] |  | 94.8 |
| Total butene selectivity [%] |  | 99.1 |

The catalyst had a very high activity. In use, it enabled high space velocities to be employed while at the same time achieving a high conversion. Compared with the catalyst from Example 11, the total butene selectivity is somewhat improved and is above 99%. No hydrogenation of the i-butene took place.

EXAMPLE 14

Using a method similar to Example 12, metal mesh made of material No. 1.4767 was heated in air at 1000° C. for 5 hours. After cooling, the support mesh was coated with 50 nm of Mg in the vacuum coating unit described. The thickness of the layer was measured during the vapor deposition procedure using a crystal oscillator. The mesh was subsequently heated to 300° C. over a period of 60 minutes and left at this temperature in air for 30 minutes. After again being installed in the coating unit, it was coated with 6 nm of Pd at $1 \times 10^{-6}$ torr. 5 monoliths were fabricated from the catalyst mesh thus obtained using a method similar to Example 10 and these were installed in the hydrogenation reactor.

EXAMPLE 15

Liquid-phase hydrogenation of raw $C_4$ fraction from a steam cracker

The catalyst produced as described in Example 14 was likewise tested in the unit described in Example 11. Before commencement of the experiment, the catalyst was reduced with hydrogen at 100° C. and 5 bar pressure for 12 hours in a manner similar to Example 11. The unit was subsequently run up using hydrogenated $C_4$ fraction and hydrogen. The results of the experiment on the selective hydrogenation are summarized in Table 5 below.

TABLE 5

|  | Starting material | Pd/MgO catalyst from Example 14 |
|---|---|---|
| Space velocity [m³/m³h] |  | 9.0 |
| Recycle/Feed |  | 8.2 |
| $T_{in}$ [°C.] |  | 60 |
| p [bar] |  | 16.3 |
| Ratio of $H_2$/(butadiene + butenyne + butyne) |  | 0.97 |
| Butadiene + butenyne + Butyne [% by weight] | 44.1 | 2.9 |
| 1-butene [% by weight] | 14.2 | 39.7 |
| 2-trans-butene [% by weight] | 4.6 | 17.4 |
| 2-cis-butene [% by weight] | 3.3 | 5.8 |
| i-butene [% by weight] | 23.6 | 23.9 |
| i-butane [% by weight] | 2.9 | 2.9 |
| n-butane [% by weight] | 7.1 | 7.5 |
| $C_5$ hydrocarbons [% by weight] | 0.2 | 0.2 |
| Conversion [%] |  | 93.4 |
| Total butene selectivity [%] |  | 99.0 |

The catalyst likewise displayed a high activity and enabled a high space velocity to be employed while at the same time achieving a high conversion. The performance data are similar to those of the catalyst from Example 13. No hydrogenation of the i-butene took place.

As shown by the examples, the catalysts of the present invention are very suitable for the selective hydrogenation of multiply unsaturated hydrocarbons.

Liquid-phase hydrogenation of butadiene-containing raffinate 1 from a steam cracker

COMPARATIVE EXAMPLE 3

A Pd,Ag/$Al_2O_3$ catalyst produced as described in DE-A-31 19 850, Example 3, was used as a comparative catalyst in the liquid-phase hydrogenation of butadiene-containing raffinate 1 from a steam cracker. The selective hydrogenation of the butadiene was carried out in the pilot plant unit described in Example 11.

Before commencement of the experiment, the Pd,Ag comparative catalyst was reduced with hydrogen at 120° C. and 5 bar pressure for 12 hours. The pilot plant was subsequently run up using butadiene-containing raffinate 1 and hydrogen. The results of this experiment are summarized in Table 6.

EXAMPLE 16

To produce the catalyst according to the present invention, plain-woven wire mesh made of material No. 1.4301 and having a mesh opening of 0.180 mm and a wire diameter of 0.105 mm was heated in air at 800° C. for 3 hours. After cooling, the support mesh which had been pretreated in this way was coated with 5 nm of Pd and 1 nm of Ag by sputtering in a rollcoater. Monoliths were subsequently produced from the catalyst mesh. For this purpose, a 20 cm-wide mesh strip was corrugated by means of a toothed roller (modulus 0.5 mm) and, using a method similar to Example 10, five monoliths having a diameter of 16 mm, a height of 20 cm and an internal thermocouple hole having a diameter of 4.5 mm were produced. The amount of catalyst mesh for one monolith was 1180 cm². The five monoliths were finally installed in the hydrogenation reactor which is described in Example 11.

Before commencement of the experiment, the Pd,Ag catalyst according to the present invention was reduced with hydrogen at 120° C. and 5 bar pressure for 12 hours. The pilot plant was subsequently run up using butadiene-containing raffinate 1 and hydrogen. The results of this experiment are summarized in Table 6.

EXAMPLE 17

To produce the catalyst according to the present invention, plain-woven wire mesh made of the material No. 1.4767 and having a mesh opening of is 0.18 mm and a wire diameter of 0.112 mm was heated in air at 900° C. for 5 hours. After cooling, the support mesh which had been pretreated in this way had first 4 nm of Pd and then 2 nm of Ag vapor-deposited on both sides at a reduced pressure of $1\times10^{-6}$ torr. The thickness of the layers was measured by means of a crystal oscillator and the vapor deposition rate was controlled using the crystal oscillator. Monoliths were subsequently produced from this catalyst mesh. For this purpose, a 20 cm-wide mesh strip was corrugated by means of a toothed roller (modulus 0.5 mm) and, using a method similar to Example 10, five monoliths having a diameter of 16 mm, a height of 20 cm and an internal thermocouple hole having a diameter of 4.5 mm were produced. The amount of catalyst mesh for one monolith was 940 cm². The five monoliths were finally installed in the hydrogenation reactor which is described in Example 11.

Before commencement of the experiment, the Pd,Ag catalyst according to the present invention was reduced with hydrogen at 120° C. and 5 bar pressure for 12 hours. The pilot plant was subsequently run up using butadiene-containing raffinate 1 and hydrogen. The results of this experiment are summarized in Table 6.

Table 6 shows a performance comparison for the conventional catalyst from Comparative Example 3 and the two catalysts according to the present invention from Examples 16 and 17. As can be seen, the catalyst according to the present invention from Example 16 gives a 1-butene yield which is about 3% higher than that obtained using the comparative catalyst described at the same final butadiene content in the hydrogenated product of 20 ppm. The advantages of the monolithic catalyst according to the present invention from Example 17 are considerably more pronounced, with a residual butadiene content in the hydrogenated product of 10 ppm being achieved. The 1-butene yield obtained here was over 97%.

The performance data reveal four significant advantages of the catalyst according to the present invention over the comparative catalyst described:

(i) smaller $H_2$/butadiene ratio (1.6 instead of 1.9 for the comparative catalyst)

(ii) less overhydrogenation to give n-butane (n-butane formation of 0.4% by weight instead of 0.8% by weight for the comparative catalyst)

(iii) significantly higher 1-butene yield (97.4% instead of 89.2% for the comparative catalyst)

(iv) significantly lower active component content as high activity (12.3 mg of active component in the amount of catalyst used instead of 480 mg for the comparative catalyst).

In all examples, no hydrogenation of the i-butene was found.

EXAMPLE 18

The conventional comparative catalyst described in Comparative Example 3 and the catalyst according to the present invention described in Example 17 were likewise tested under more severe hydrogenation conditions in the pilot plant unit described in Example 11. Under these conditions, a residual butadiene content in the hydrogenated product of <10 ppm was able to be achieved. The results obtained are summarized in Table 7.

TABLE 7

|  | Conventional Pd, Ag/Al$_2$O$_3$ catalyst from Comparative Example 3 | | Pd, Ag catalyst from Example 17 | |
| --- | --- | --- | --- | --- |
|  | Feed | Hydrogenation product | Feed | Hydrogenation product |
| Space velocity [m³/m³h] |  | 15 |  | 15 |
| Recycle/feed |  | 1 |  | 1 |
| T$_{in}$ [°C.] |  | 60 |  | 60 |
| p [bar] |  | 11.9 |  | 11.3 |
| H$_2$/butadiene ratio |  | 2.7 |  | 2.1 |
| Butadiene [% by weight] | 0.43 | <0.001 | 0.54 | <0.001 |
| 1-Butene [% by weight] | 25.1 | 20.8 | 27.2 | 25.9 |
| trans-2-Butene [% by weight] | 7.9 | 10.2 | 8.4 | 9.0 |
| cis-2-Butene [% by weight] | 5.4 | 7.1 | 5.7 | 6.3 |
| i-Butene (% by weight] | 42.2 | 42.2 | 43.9 | 43.9 |
| i-Butane [% by weight] | 4.7 | 4.7 | 3.0 | 3.0 |
| n-Butane [% by weight] | 14.0 | 14.8 | 11.0 | 11.7 |
| C$_5$ hydrocarbons [% by weight] | 0.27 | 0.2 | 0.26 | 0.2 |
| Conversion [%] |  | >99.8 |  | >99.8 |
| n-Butane formation [% by weight] |  | 0.8 |  | 0.7 |
| 1-Butene yield [%] |  | 82.9 |  | 95.2 |

In a hydrogenation to butadiene values of <10 ppm, the catalyst according to the present invention likewise shows the abovementioned advantages of a small $H_2$/butadiene ratio, less overhydrogenation to give n-butane and a significantly higher 1-butene yield. As in the previous examples, no hydrogenation of i-butene was found in this case.

TABLE 6

| | Conventional Pd, Ag/Al$_2$O$_3$ catalyst from Comparative Example 3 | | Pd, Ag catalyst from Example 16 | | Pd, Ag catalyst from Example 17 | |
| --- | --- | --- | --- | --- | --- | --- |
| | Feed | Hydrogenation product | Feed | Hydrogenation product | Feed | Hydrogenation product |
| Space velocity [m$^3$/m$^3$h] | | 15 | | 15 | | 15 |
| Recycle/feed | | 1 | | 1 | | 1 |
| T$_{in}$ [°C.] | | 60 | | 60 | | 60 |
| p [bar] | | 11.8 | | 11.5 | | 11.3 |
| H$_2$/butadiene ratio | | 1.9 | | 1.9 | | 1.6 |
| Butadiene [% by weight] | 0.46 | 0.002 | 0.50 | 0.002 | 0.54 | 0.001 |
| 1-Butene [% by weight] | 25.0 | 22.3 | 27.7 | 25.6 | 27.2 | 26.5 |
| trans-2-Butene [% by weight] | 7.8 | 9.1 | 8.4 | 9.4 | 8.4 | 8.9 |
| cis-2-Butene [% by weight] | 5.4 | 6.4 | 5.7 | 6.5 | 5.7 | 6.1 |
| i-Butene [% by weight] | 42.9 | 42.9 | 43.6 | 43.5 | 43.9 | 43.9 |
| i-Butane [% by weight] | 4.6 | 4.6 | 3.2 | 3.2 | 3.0 | 3.0 |
| n-Butane [% by weight] | 13.6 | 14.4 | 10.6 | 11.5 | 11.0 | 11.4 |
| C$_5$ hydrocarbons [% by weight] | 0.24 | 0.3 | 0.3 | 0.3 | 0.26 | 0.2 |
| Conversion [%] | | 99.6 | | 99.6 | | 99.8 |
| n-Butane formation [% by weight] | | 0.8 | | 0.9 | | 0.4 |
| 1-Butene yield [%] | | 89.2 | | 92.4 | | 97.4 |

We claim:

1. A process for the hydrogenation of C$_2$–C$_8$-alkynes and/or C$_4$–C$_8$-alkynenes and/or C$_4$–C$_8$-alkadienes in fluids comprising these by contact with a catalyst packing in the presence of free hydrogen, wherein the catalyst packing is produced by coating woven or knitted meshes or foils acting as support material with at least one substance acting as catalyst or catalyst and promoter.

2. A process as claimed in claim 1, wherein the substance or substances active as catalyst and/or promoter is/are applied by vapor deposition and/or sputtering or impregnation.

3. A process as claimed in claim 1, wherein the catalyst packing comprises at least one monolith which is fabricated from the woven or knitted mesh or foil which is preferably in the form of a strip.

4. A process as claimed in any of the claim 1, wherein the woven or knitted mesh or foil comprises metal or inorganic material.

5. A process as claimed in claim 4, wherein the woven or knitted metal mesh or foil is, prior to vapor deposition and/or sputtering, heated at from 400° to 1100° C. in an oxygen-containing atmosphere for from 0.5 to 24 hours.

6. A process as claimed in claim 1, wherein the substances active as catalyst are selected from among the elements of transition groups I and/or VII and/or VIII and/or the promoters are selected from among the elements of main groups III, IV, V, and VI and transition groups II, III, VI and VII of the Periodic Table of the Elements.

7. A process as claimed in claim 1, wherein the fluids are C$_2$, C$_3$, C$_4$, C$_5$ or C$_6$ streams, preferably from a steam cracker, or a catalytic cracker, in which the corresponding multiply unsaturated hydrocarbons, in particular alkynes and/or alkynenes and/or alkadienes, are present.

8. A process as claimed in claim 1, wherein the hydrogenation, preferably of C$_2$ and/or C$_3$ streams, is carried out in the gas phase.

9. A process as claimed in claim 1, wherein the hydrogenation, preferably of C$_3$, C$_4$, C$_5$ and/or C$_6$ streams, is carried out in the liquid phase or in a mixed liquid/gas phase having at least 50% by weight of the fluid in the liquid phase.

10. A process for catalytic distillation in which a hydrogenation as defined in claim 1 is combined with a simultaneous distillation or rectification over the catalyst packing, wherein the fluids cn be C$_3$, C$_4$, C$_5$ and/or C$_6$ streams.

* * * * *

UNITED STATES PATENT AND TRADEMARK OFFICE
CERTIFICATE OF CORRECTION

PATENT NO. : 5,866,734
DATED : February 2, 1999
INVENTOR(S) : FLICK et al.

It is certified that error appears in the above-identified patent and that said Letters Patent is hereby corrected as shown below:

On the cover page, item [73], the assignee name should be:
--BASF Aktiengesellschaft, Ludwigshafen, Germany--, Signed and Sealed this Fifteenth Day of June, 1999

Attest:

Q. TODD DICKINSON

Attesting Officer

Acting Commissioner of Patents and Trademarks